US008088322B2

(12) United States Patent
Arkenau-Maric et al.

(10) Patent No.: US 8,088,322 B2
(45) Date of Patent: Jan. 3, 2012

(54) METHOD AND DEVICE FOR ULTRASOUND-PRESSING A TABLET OR A MULTIPARTICULATE MEDICAMENT

(75) Inventors: Elisabeth Arkenau-Maric, Cologne (DE); Johannes Bartholomaeus, Aachen (DE); Anja Geissler, Stolberg/Vicht (DE); Rene Jansen, Eschweiler (DE)

(73) Assignee: Gruenenthal GmbH, Aachen (DE)

( * ) Notice: Subject to any disclaimer, the term of this patent is extended or adjusted under 35 U.S.C. 154(b) by 894 days.

(21) Appl. No.: 11/909,364

(22) PCT Filed: Mar. 22, 2006

(86) PCT No.: PCT/EP2006/060965
§ 371 (c)(1),
(2), (4) Date: Apr. 3, 2008

(87) PCT Pub. No.: WO2006/100274
PCT Pub. Date: Sep. 28, 2006

(65) Prior Publication Data
US 2008/0213358 A1    Sep. 4, 2008

(30) Foreign Application Priority Data

Mar. 22, 2005  (DE) .......................... 10 2005 013 725
May 23, 2005  (DE) .......................... 10 2005 024 171

(51) Int. Cl.
   *B29C 43/36*   (2006.01)
(52) U.S. Cl. ....... 264/443; 264/494; 425/78; 425/174.2; 424/464; 424/489

(58) Field of Classification Search .................. 424/465, 424/466, 489, 486, 487, 488, 484, 425, 443, 424/456; 425/78, 174.2, 344–345; 264/405, 264/407, 442, 443, 494
See application file for complete search history.

(56) References Cited

U.S. PATENT DOCUMENTS 5,662,935 A * 9/1997 Motta ........................... 424/465
5,919,493 A * 7/1999 Sheppard et al. .......... 425/174.2
2005/0236741 A1 10/2005 Arkenau et al.

FOREIGN PATENT DOCUMENTS

| CH | 486 317 A | 2/1970 |
| DE | 41 06 645 A1 | 9/1992 |
| DE | 199 45 155 A1 | 6/2001 |
| DE | 10 2004 020 220 A1 | 11/2005 |
| JP | 63-275511 A | 11/1988 |

(Continued)

OTHER PUBLICATIONS

Levina et al., Principles and Application of Ultrasound in Pharmaceutical Powder Compression, 2000, Pharmaceutical Research, pp. 257-265.*

(Continued)

*Primary Examiner* — Richard Crispino
*Assistant Examiner* — Thukhanh Nguyen
(74) *Attorney, Agent, or Firm* — Crowell & Moring LLP (57) ABSTRACT

The present invention relates to a method and a device for shaping a pharmaceutically active substance in the form of powders, granules, multiparticulate medicaments, in particular pellets and microcapsules, for the production of a tablet or a multiparticulate medicament by means of ultrasound, with an ultrasound generator, a sonotrode and a mould, into which the pharmaceutically active substance can be poured.

18 Claims, 6 Drawing Sheets

FOREIGN PATENT DOCUMENTS

| | | |
|---|---|---|
| JP | 6-220504 A | 8/1994 |
| WO | WO 95/10407 A1 | 4/1995 |
| WO | WO 01/21388 A1 | 3/2001 |

OTHER PUBLICATIONS

International Search Report (in English) dated Jul. 4, 2006 (three (3) pages).

German Search Report dated Dec. 2, 2005 w/English translation (Nine (9) pages).

International Preliminary Examination Report included Amended Claims (PCT/IPEA/416 and 409) dated Jul. 23, 2007 and an English translation of the Amended Claims Only (Fifteen (15) pages).

International Preliminary Report on Patentability (Pct/IB/338 and IPEA 409) dated Mar. 13, 2008 Nine (9) pages.

\* cited by examiner

METHOD AND DEVICE FOR ULTRASOUND-PRESSING A TABLET OR A MULTIPARTICULATE MEDICAMENT

The present invention relates to a method and a device for shaping a pharmaceutically active substance, in particular a drug, in the form of powders, granules or multiparticulate medicaments, such as, for example, pellets and microcapsules, for the production of a tablet or a multiparticulate medicament by means of ultrasound comprising an ultrasound generator, a sonotrode and a mould, into which the pharmaceutically active substance can be poured.

Ultrasound devices of this kind for melting and pressing tablets are known from the prior art and are described, for example, in the article "Principles and Application of Ultrasound in Pharmaceutical Powder Compression", Pharmaceutical Research, Vol. 17, No 3, 2000, page 257-265. This article is hereby introduced as a reference and is therefore deemed to be part of the disclosure. However, the tabletting by means of ultrasound described in the prior art has the drawback that, when using ultrasound, the sonotrode, the lower die and/or the mould are subject to extremely high wear and/or that the lower die and/or the mould and/or parts of the ultrasound device are spot welded together. In order to avoid this, the prior art suggests, for example, that the parts be separated from each other by films. However, in practice this has been found to be very complex, difficult to manipulate and cost-intensive.

It was therefore the object of the present invention to provide a device for shaping a pharmaceutically active substance, in particular a drug, in the form of powders, granules or multiparticulate medicaments, such as, for example, pellets and microcapsules, for the production of a tablet or a multiparticulate medicament by means of ultrasound which does not have the drawbacks of the prior art.

The object is achieved with a device for shaping a pharmaceutically active substance, in particular a drug, in the form of powders, granules or multiparticulate medicaments, such as, for example, pellets and microcapsules, for the production of a tablet or a multiparticulate medicament by means of ultrasound, with an ultrasound generator, a sonotrode and a mould into which the pharmaceutically active substance can be poured, wherein, during the shaping, the sonotrode is in direct contact with the pharmaceutically active substance and there is no direct contact between the sonotrode and the mould.

It was extremely surprising and unexpected for the person skilled in the art that the device according to the invention can be produced and operated simply and inexpensively. The service lives of the sonotrode and the mould are significantly increased. The device according to the invention can be used to produce a tablet or a multiparticulate medicament with which the abuse of a tablet of this kind, which, for example, contains psychotropic substances, is at least significantly impeded. A hard tablet of this kind also serves to avoid the faulty use of medicaments with highly active substances, because, due to their hardness, tablets of this kind cannot be comminuted by means of a comminuter, for example, a mortar. Comminution of this kind or generally the destruction of the mechanical structure of the tablet can in fact greatly impair the pharmacological efficacy, in particular the temporal course of the release of the highly active substance, in particular with a so-called delayed-release formulation. During the production of a tablet or a multiparticulate medicament by means of the device according to the invention, no films or other separating agents are required between the sonotrode and the pharmaceutical substance that is to be compacted.

The device according to the invention is suitable for shaping a pharmaceutically active substance, in particular for shaping powders, granules, multiparticulate medicaments, such as, for example, pellets and microcapsules, for the production of a tablet or a multiparticulate medicament using ultrasound. For the purposes of the invention, shaping means that pharmaceutically active substances as starting substances, in particular as powdered drugs, are brought into the desired shape and in this regard at least partially compacted. The use of ultrasound causes the starting substances, ie in particular powdered drugs, to be heated and in this regard to melt at least partially. The starting substances melted in this way form a bond. Under a certain pressure, compaction and additional hardening of the resultant tablet or of the resultant multiparticulate medicament take place. For the purposes of the invention, a pharmaceutically active substance is a substance, which, on the one hand, has the desired pharmaceutical effect and, on the other, is suitable for the shaping by means of the device according to the invention. This means that, according to the invention the pharmaceutically active substance can quite possibly comprise a plurality of substances (and, as a rule, will actually do so), of which one part is predominantly or exclusively responsible for the pharmaceutical action and of which another part in the device according to the invention may be melted and welded or sintered together in such a way that this results in the formation of a bond or a matrix for the extensive mechanical incorporation of the pharmaceutically active part of the substances.

Furthermore, according to the invention, the device according to the invention comprises an ultrasound generator, which generates the ultrasound frequencies, which preferably fluctuate in a bandwidth between 10 and 70 kHz, particularly preferably between 10 and 40 kHz. These ultrasound frequencies are optionally amplified and then sent to a so-called sonotrode, which oscillates in the ultrasound range and delivers the oscillation energy to the starting substances that are to be shaped. The sonotrode is preferably made of high-grade steel, titanium, hardened titanium or of an alloy containing at least one of the substances named.

Furthermore, according to the invention, the device according to the invention comprises a mould into which the pharmaceutically active substance (in the time before its shaping) is poured, wherein the mould at least partially represents the negative of the tablet shape to be achieved. The mould is preferably produced from a material, which, on the coupling-in of ultrasound, does not enter into a connection with the mixture that is to be tabletted, ie with the pharmaceutically active substance intended for compaction and which does not tear or crack during the welding or shaping process (as would be the case with glass, for example). Preferably, the mould with properties of this kind is produced from ceramic, high-grade steel, titanium, high-melting plastic and/or hardened titanium.

According to the invention, the device according to the invention is now designed so that although the sonotrode is in direct contact with the pharmaceutically active substance during the shaping, at no time of the shaping is there direct contact between the mould and the sonotrode. This means, on the one hand, it is possible to achieve the desired tablet or the desired multiparticulate medicament with the desired shape and the desired hardness but, on the other, the aforementioned spot welding does not take place.

Preferably, there is a gap between the sonotrode and the mould, of which the maximum size is dimensioned so that none of the pharmaceutically active substance can escape through it, in particular at the start of the ultrasound shaping.

Preferably, the gap has a size of less than 2 mm, preferably less than 1 mm, and particularly preferably less than 0.7 mm.

In a further preferred embodiment, a spacer is disposed between the sonotrode and the mould. This preferred embodiment of the present invention is in particular of advantage when the sonotrode is moved during the shaping of the pharmaceutically active substance, in order, for example, to ensure that, even in the case of a pharmaceutically active substance which consolidates during the shaping, there is always good contact between the pharmaceutically active substance and the sonotrode and/or in order to be able to perform the ultrasound-assisted shaping under pressure. With this embodiment, there is a risk of the sonotrode penetrating the mould and hence of direct contact between the sonotrode and the mould being established which would result in spot welding and/or the destruction of the sonotrode. The contact formation is prevented by the spacer, which ensures a constant distance between the sonotrode and the mould.

Preferably, as already mentioned, the sonotrode is axially displaceable. This preferred embodiment of the present invention is in particular of advantage when the sonotrode is exposed to a certain pressure load and the pharmaceutically active substance is compacted during the shaping.

It is also preferred that the mould is also displaceably mounted or that the mould has a pre-opening.

Quite particularly preferred, the movement of the sonotrode and the mould is uniform after the gap has been set. This ensures that the gap is neither reduced nor enlarged so that neither powdered nor molten drug powder—ie parts of the pharmaceutically active substance before its final shaping—are able to escape through the gap and that the sonotrode is not destroyed and/or that the mould and lower die are not spot welded to each other.

In a further preferred embodiment, the device according to the invention comprises a die, which is disposed on the side of the mould opposite to the sonotrode. In this case, the mould is preferably only designed in an annular shape and the volume, into which the pharmaceutically active substance is poured before shaping according to the invention, is delimited from below by a die. Preferably, this die is mounted so that when the ultrasound is coupled into the pharmaceutically active substance, the die does not co-oscillate or only co-oscillates to an extent that a material connection between the die and the mould can be excluded. This is preferably achieved by the fact that the die is mounted in a sound-reflecting component preferably in a positive and/or non-positive connection. Preferably, the die is mounted in an axially displaceable manner. This embodiment has in particular the advantage that the sonotrode can be designed as fixed during the ultrasound shaping and the pressure optionally required for the shaping can be introduced through the die into the pharmaceutically active substance. In addition, the die is preferably mounted so that depth of penetration into the mould can be adjusted. This embodiment has in particular the advantage that the volume or the quantity of the pharmaceutically active substance, which is poured into the mould and then exposed to shaping, can be adjusted.

As already mentioned, it is usually of advantage for the shaping to be performed by means of ultrasound and under exposure to a certain force during the ultrasound coupling, wherein the force is preferably up to 10 kN, particularly preferably up to 5 kN and quite particularly preferably up to 2 kN. This force can be transmitted by the sonotrode and/or by a die to the powdered drug, ie the pharmaceutically active substance.

The duration of the ultrasound treatment or the temperature profile is determined in particular by the desired result and will be determined experimentally by the person skilled in the art.

Further subject matter of the present invention is a method for shaping a pharmaceutically active substance, in particular a drug, in the form of powders, granules or multiparticulate medicaments, such as, for example, pellets and microcapsules, for the production of a tablet or a multiparticulate medicament by means of ultrasound, with an ultrasound generator, a sonotrode and a mould, into which the pharmaceutically active substance can be poured, with which the sonotrode and the mould are moved in such a way during the shaping that a gap is always maintained between the sonotrode and the mould and the sonotrode is in direct contact with the pharmaceutically active substance, preferably drug, that is to be plasticised or compacted during the shaping.

Further subject matter of the present invention is a method for shaping a pharmaceutically active substance, in particular a drug, in the form of powders, granules or multiparticulate medicaments, such as, for example, pellets and microcapsules, for the production of a tablet or a multiparticulate medicament by means of ultrasound with an ultrasound generator, a sonotrode and a mould, into which the pharmaceutically active substance, in particular the powdered drug, can be poured, wherein in the method, during the welding, the sonotrode is in direct contact with the drug, ie the pharmaceutically active substance, and there is a gap between the sonotrode and the mould and that during the welding a die is moved in the direction of the sonotrode.

Both methods according to the invention are simple and inexpensive to perform and are suitable for the production of tablets with high hardness comprising, for example, psychotropic substances and with which faulty use or simple abuse can be excluded.

Further subject matter of the present invention is therefore the use of the device according to the invention and/or the method according to the invention for the production of drugs of this kind, in particular tablets or multiparticulate medicaments containing psychotropic substances and which are not subject to medical prescription as narcotic drugs or which have a high degree of hardness so that faulty use is reliably avoided.

All the above statements apply equally to the device according to the invention and the method according to the invention and the use according to the invention.

The following describes the invention with reference to FIGS. 1-5. These explanations are by way of example only and do not restrict the general concept of the invention. The explanations apply equally to the device according to the invention, the method according to the invention and the use according to the invention.

Figure 1:
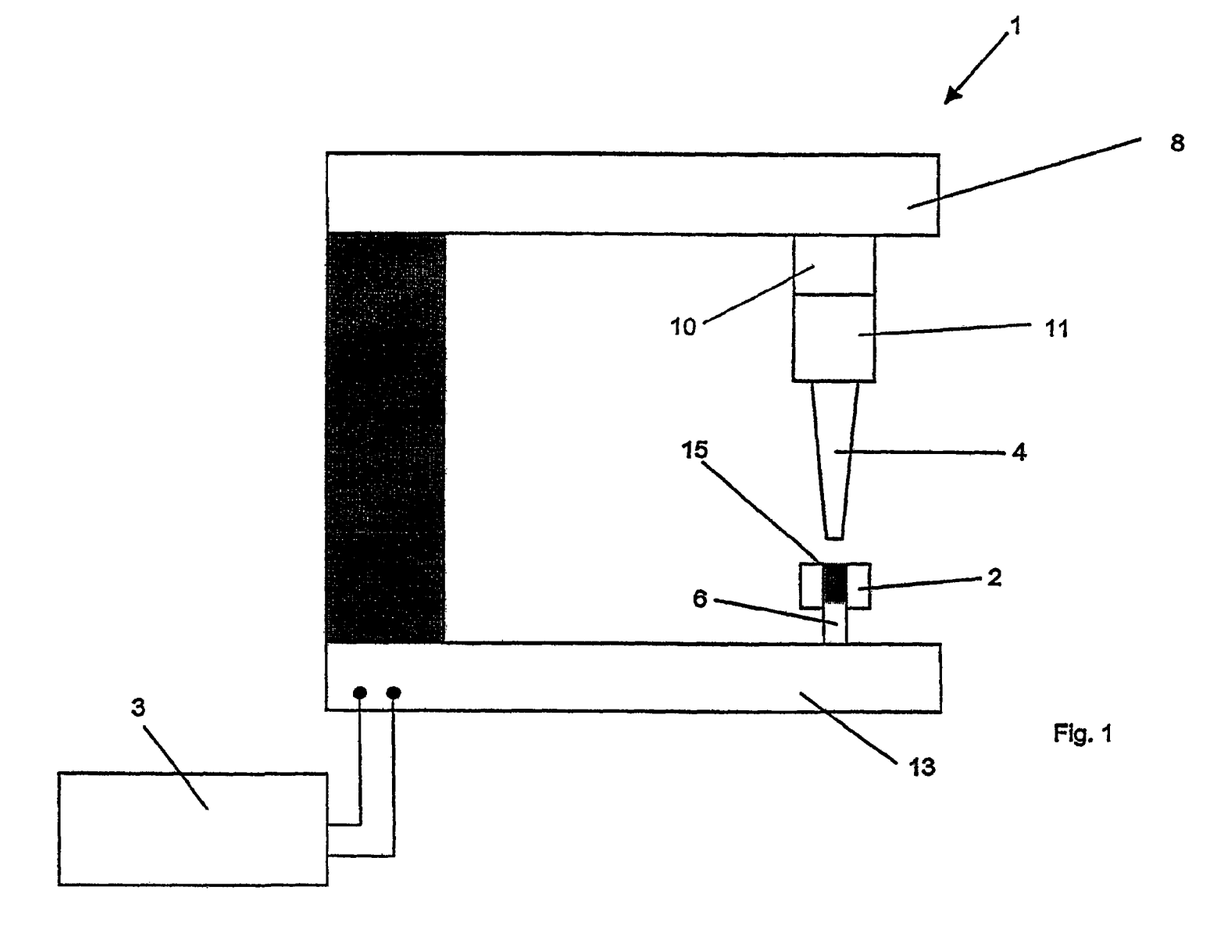
FIG. 1 shows a schematic diagram of the device according to the invention.

FIG. 1 shows an embodiment of the device 1 according to the invention. The device 1 comprises a sonotrode 4, which is connected to an amplifier 11 which in turn, by means of a converter 10, for example, a piezoelement, converts the electrical signals from the generator 3 into oscillations which are amplified by the amplifier 11 and forwarded to the sonotrode 4. In addition, the device 1 comprises a press 8, with which the sonotrode 4 can be pressed vertically downward with a certain pressure. In addition, the device according to the invention comprises a mould 2, which is connected to a die 6. The mould 2 and the die 6 define an interior space, which may be filled with a pharmaceutically active substance 15. The die 6 is mounted in a sound-reflecting base plate 13 so that during the coupling-in of the ultrasound into the pharmaceutically active substance 15 it does not co-oscillate, or only co-oscillates such that no spot welding occurs between the mould 2 and the die 6. During the welding or sintering process of the pharmaceutically active substance, during which, according to the invention, the shaping takes place simultaneously, the lower die is held in a position, which is suitable for performing the method according to the invention, in particular in such a way that the die and the mould are not welded together or that the tablet has the desired volume. The force for the compaction of the product is applied via the sonotrode during and optionally also after the welding process.

Figure 2:
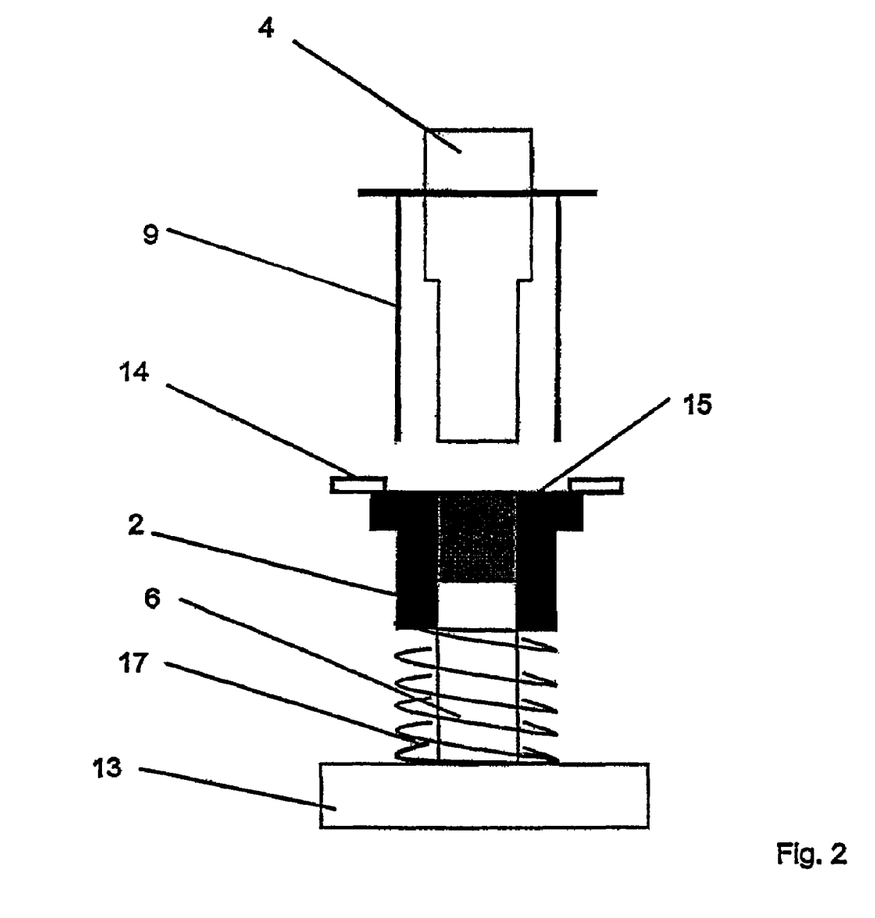
FIG. 2 shows a detailed representation of the device according to the invention in particular of the shaping.

FIG. 2 shows the die-mould sonotrode disposal in detail. It may be identified that attached to the sonotrode 4 there is a spacer 9 which moves up and down together with the sonotrode 4. It may also be identified that the mould 2 is mounted displaceably relative to the die 6 and that disposed between the mould 2 and the base plate 13 is a spring 17 which presses the mould 2 upward against a limiting means 14. The state shown in FIG. 2 is the configuration before the shaping of a tablet 19 not shown in FIG. 2. The interior space defined by the mould 2 and the die 6 is filled with the pharmaceutically active substance 15. The location of the die 6 can be changed relative to the mould 2 in order to change the volume to be filled with the pharmaceutically active substance 15. This can take place, for example, by disposing a thread in the mould 2 or the base plate 13 corresponding to a thread in the die 6. Turning the die 6 enables the volume available for the drug powder to be changed. In the present case, the sonotrode 4 is made of hardened titanium. The mould 2 can be made of high-grade steel, titanium, hardened titanium, high-melting plastic or ceramics.

Figure 3:
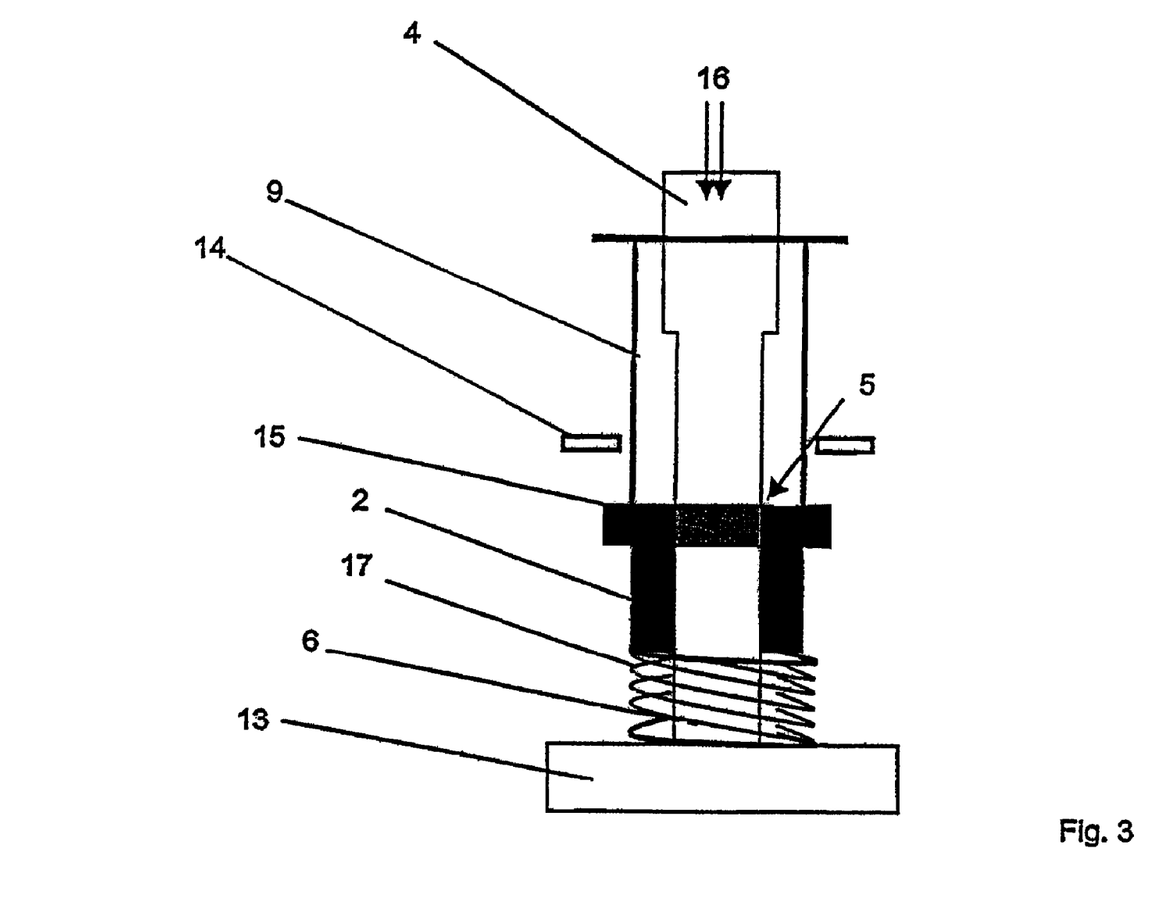
FIG. 3 shows a detail of the device according to the invention during the shaping.

FIG. 3 shows the shaping of a tablet. The oscillations of the sonotrode 4 in the ultrasound frequency range and the pressure 16 indicated by the double arrow acting on the sonotrode 4 cause the volume of the pharmaceutically active substance 15 to be compacted so that the sonotrode 4 moves downward during the shaping, ie during the compaction, and the welding of the pharmaceutically active substance 15 for the production of the tablet. The spacer 9, which is firmly connected to the sonotrode 4 and the under end of which interacts with the mould 2, also presses the mould downward during the downward movement of the sonotrode 4 so that the annular gap 5, which is disposed between the lower end of the sonotrode 4 and the mould 2 and which may be adjusted by the spacer 9, does not change throughout the entire shaping process. The gap 5 is set so that the sonotrode 4 does not touch the mould 2 but that it is ensured that during the shaping no pharmaceutically active substance, be it in its original shape (powder, granules, multiparticulate) or in an intermediate shape (for example, in molten form), escapes from the device 1 according to the invention during the performance of the method according to the invention and that the sonotrode 4 is in continuous contact with the pharmaceutically active substance 15 that is to be processed. The downward movement of the mould 2 compresses the spring 17.

Figure 4:
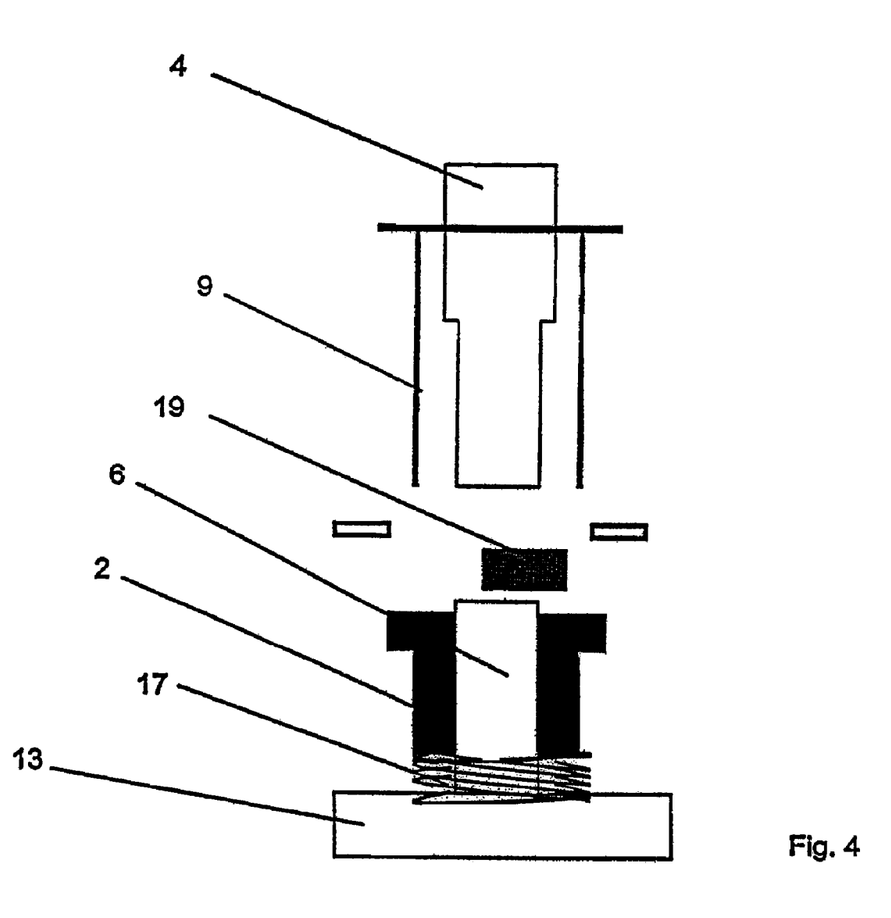
FIG. 4 shows the representation according to FIG. 3 after the completion of the tablet.

FIG. 4 shows the ejection of the tablet 19. When the tablet 19 is finished, the mould 2 is pushed still further downward until its upper edge is at least at the same height as the upper edge of the die 6 and held in this position for a short moment. Simultaneously, the sonotrode 4, and hence the spacer 9, is moved upward. The tablet 19 now only lies on the die 6 and can therefore be easily removed. As soon as the tablet 19 is removed, the mould 2 shoots back upward until it strikes the travel limiter 14 and the volume created in this way can be filled again with pharmaceutically active substance 15, after which this new filling of pharmaceutically active substance 15 can—as described with reference to FIGS. 2 and 3—also be compacted and welded. The person skilled in the art will recognise that the removal of the tablet 19 from the mould can also be performed by lifting the die 6.

Figure 5:
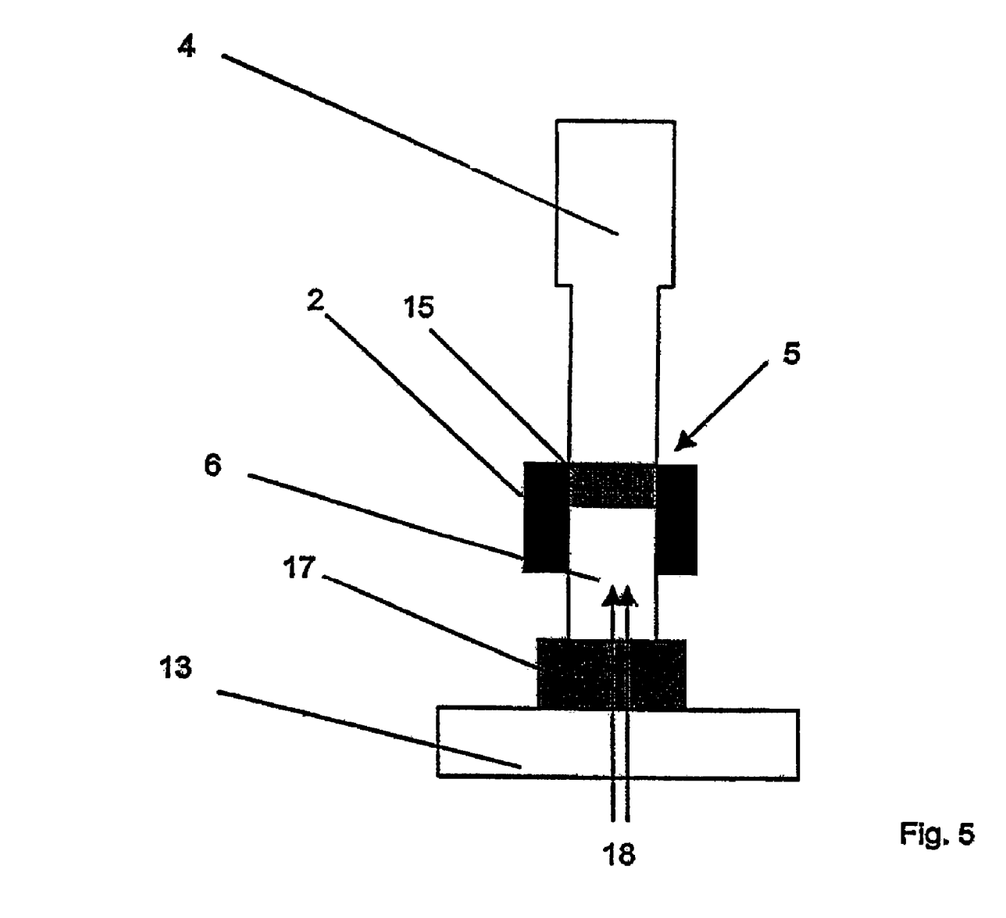
FIG. 5 shows a further embodiment of the device according to the invention.

FIG. 5 shows another embodiment of the device according to the invention. In this case, the sonotrode 4 is disposed in a stationary manner during the shaping so that an annular gap 5 is present between the sonotrode 4 and the mould 2 which satisfies the aforementioned criteria. In this case, the loss of volume of the pharmaceutically active substance during the shaping is compensated by the vertically mobile die 6, which is subjected to force by the pressure means 17 with force and which moves upward during the shaping process. This die 6 is also disposed on the sound-reflecting base plate 13 or on the sound-reflecting pressure means 17 so that it does not oscillate or only oscillates so that no spot welding can occur between the die 6 and the mould 2. The demoulding and removal of the finished tablet is substantially performed as shown in FIG. 4.

Figure 6:
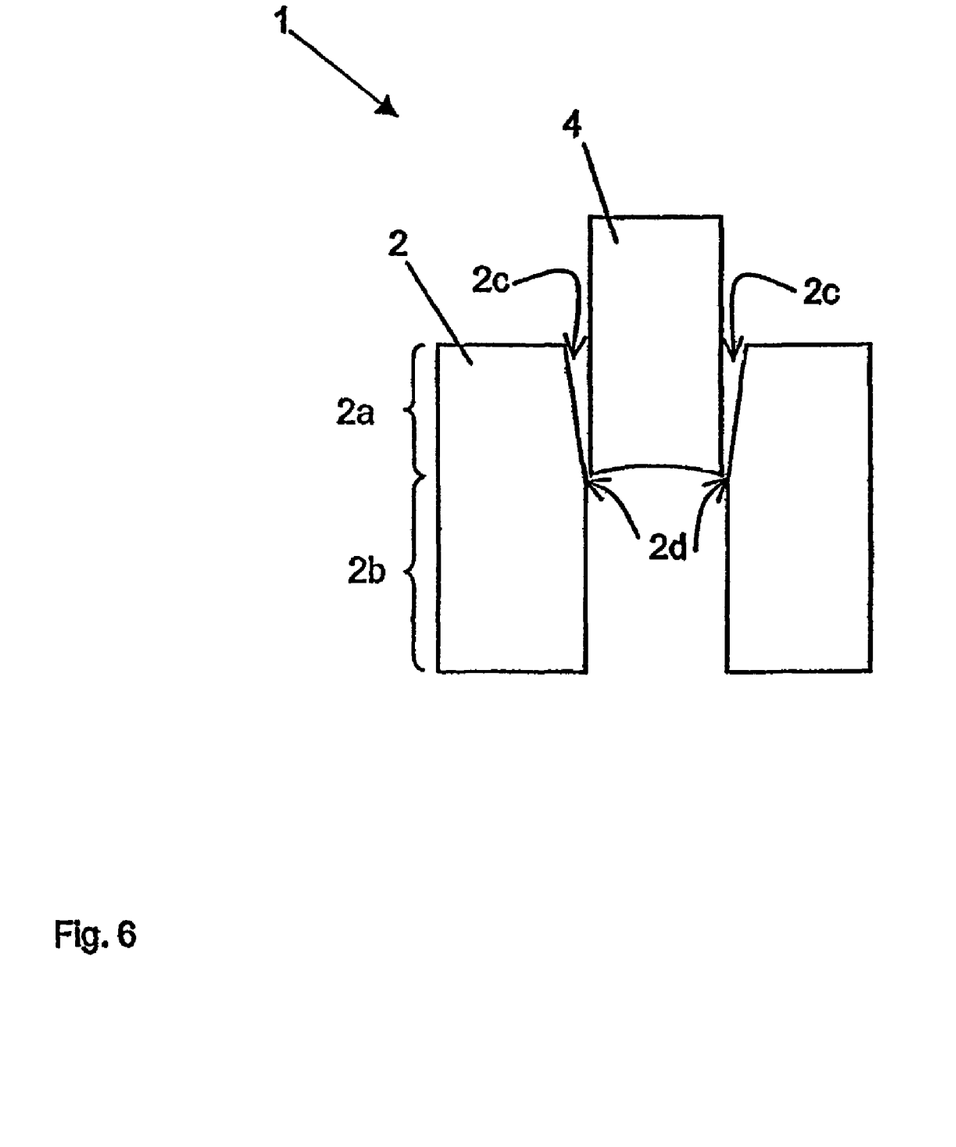
FIG. 6 shows an alternative embodiment of the device according to the invention with a pre-opening in the upper region of the mould.

FIG. 6 shows an alternative embodiment of the device 1 according to the invention with a pre-opening 2c in the upper region 2a of the mould 2. The mould 2 is depicted in FIG. 6 in a sectional representation. The mould 2 is provided cylindrically in the lower region 2b. In the region of the pre-opening 2c, the mould 2 is provided as expanding toward the sonotrode 4, in particular in a conical shape. This shaping means that according to the invention it is possible in a particularly efficient way to condense the pharmaceutically active substance 15 (not shown in FIG. 6) before it is melted or welded. Furthermore, this shaping of the mould 2 ensures it is possible in a particularly effective way to prevent air inclusions inside the pharmaceutically active substance and therefore also within the finished tablet 19 (also not shown). During the carrying out of the method for shaping according to the invention, the sonotrode 4 travels as far as shortly before the transition between the lower, preferably cylindrical, region 2b of the mould 2 and the upper region 2a, which corresponds to the pre-opening 2c. According to the invention, it is preferably provided that, at each stage of the method for shaping, the sonotrode 4 maintains a distance to this transition between the regions 2a and 2b, which can be embodied, for example, as an edge 2d, said distance preferably being smaller than 1 mm, particularly preferably smaller than 0.7 mm. The pre-opening 2c must be selected so that the sonotrode 4 does not touch the mould 2 during the coupling-in of ultrasound.

LIST OF REFERENCE NUMBERS

1 Device
2 Mould
2a Upper region of the mould
2b Lower region of the mould
2c Pre-opening
2d Edge between the upper and lower region of the mould
3 Ultrasound generator 4 Sonotrode
5 Gap
6 Die
8 Pressure means
9 Spacer
10 Converter
11 Amplifier, booster
13 Sound-reflecting base plate
14 Upper travel limit for the mould
15 Pharmaceutically active substance, in particular powdered drug
16 Pressure, axial movement of the sonotrode
17 Power transmitter (pneumatically or hydraulically driven)
18 Axial longitudinal displacement of the die 6
19 Finished tablet

The invention claimed is:

1. A device for shaping a pharmaceutically active substance in the form of powders, granules or multiparticulate medicaments and producing a tablet or a multiparticulate medicament comprising:
   an ultrasound generator;
   a sonotrode; and
   a mold configured so that a pharmaceutically active substance can be poured into the mold,
   said device being configured so that during shaping, the sonotrode is in direct contact with the pharmaceutically active substance and the sonotrode does not penetrate the mold, so that an axial gap is disposed between the lower end of the sonotrode and the mold and that there is no direct contact between the sonotrode and the mold and
   said pharmaceutically active substance is in the form of a powder or a multip articulate form.

2. A device according to claim 1, wherein said pharmaceutically active substance is in the form of pellets or microcapsules.

3. A device according to claim 1, wherein the device is configured so that said gap has a maximum size dimensioned so that no pharmaceutically active substance escapes through it.

4. A device according to claim 1, further comprising a spacer disposed between the sonotrode and the mold.

5. A device according to claim 1, wherein the sonotrode is moveable in an axial direction.

6. A device according to claim 1, wherein the mold is displaceably mounted.

7. A device according to claim 1, wherein the mold comprises a pre-opening.

8. A device according to claim 1, wherein the mold comprises an opening which is larger toward one side of the mold.

9. A device according to claim 1, wherein the movements of the sonotrode and the mold occur uniformly after the establishment of the gap.

10. A device according to claim 1, further comprising a die located on a side of the mold opposite the sonotrode.

11. A device according to claim 10, wherein the die is mounted so that when ultrasound energy is applied, the die does not co-oscillate.

12. A device according to claim 1, wherein the die is disposed movably.

13. A device according to claim 1, further comprising a press which acts on at least one of the sonotrode or the die and supports the shaping of the tablet or multiparticulate pharmaceutical formulation.

14. A device according to claim 1, further comprising a pressure means which acts on at least one of the sonotrode or the die and supports the shaping of the tablet or multiparticulate medicament.

15. A method for shaping a pharmaceutically active substance in the form of powders, granules or multiparticulate medicaments for the production of a tablet or a multiparticulate medicament comprising the steps of:
   providing a sonotrode in direct contact with the pharmaceutically active substance;
   maintaining an axial gap between the sonotrode and the mold by moving the sonotrode and the mold, wherein the sonotrode does not penetrate the mold and wherein the axial gap is disposed between the lower end of the sonotrode and the mold; and
   providing ultrasound energy to the pharmaceutically active substance to shape the pharmaceutically active substance.

16. A method according to claim 15, wherein said pharmaceutically active substance is a psychotropic substance.

17. A method for shaping a pharmaceutically active substance in the form of powders, granules or multiparticulate medicaments into a tablet or a multiparticulate medicament comprising the steps of:
   providing a sonotrode in direct contact with the pharmaceutically active substance;
   maintaining an axial gap between the sonotrode and the mold, wherein the sonotrode does not penetrate the mold and the axial gap is disposed between the lower end of the sonotrode and the mold;
   moving a die in the direction of the sonotrode; and
   providing ultrasound energy to the pharmaceutically active substance to shape the pharmaceutically active substance.

18. A method according to claim 17, wherein said pharmaceutically active substance is a psychotropic substance.

* * * * *